United States Patent [19]

Cliffe et al.

[11] Patent Number: 5,629,323

[45] Date of Patent: May 13, 1997

[54] AMIDE DERIVATIVES AS 5-HT$_{1A}$ LIGANDS

[75] Inventors: Ian A. Cliffe, Slough; Anderson D. Ifill, Oxford, both of England

[73] Assignee: John Wyeth & Brother, Ltd., United Kingdom

[21] Appl. No.: 446,651

[22] PCT Filed: Mar. 9, 1994

[86] PCT No.: PCT/GB94/00455

§ 371 Date: May 25, 1995

§ 102(e) Date: May 25, 1995

[87] PCT Pub. No.: WO94/21611

PCT Pub. Date: Sep. 29, 1994

[30] Foreign Application Priority Data

Mar. 19, 1993 [GB] United Kingdom ............. 9305672

[51] Int. Cl.$^6$ .............. C07D 401/12; C07D 213/75; C07D 407/12; A61K 31/47; A61K 31/44

[52] U.S. Cl. .............. 514/314; 514/352; 514/338; 514/339; 546/171; 546/277.4; 546/202.4; 546/330; 546/336; 546/338; 546/342; 546/329; 546/339; 546/346; 546/348

[58] Field of Search ................. 546/171, 270, 546/394, 273; 514/352, 338, 339

[56] References Cited

FOREIGN PATENT DOCUMENTS

| | | |
|---|---|---|
| A10170213 | 7/1985 | European Pat. Off. . |
| A10367888 | 11/1988 | European Pat. Off. . |
| A20512755 | 4/1992 | European Pat. Off. . |
| WO9206082 | 10/1991 | WIPO . |

*Primary Examiner*—David B. Springer
*Attorney, Agent, or Firm*—R. F. Boswell, Jr.

[57] ABSTRACT

Amide Derivatives of formula (I) wherein $R^1$ is a mono or bicyclic heteroaryl radical, $R^2$ is cycloalkyl, $R^3$ and $R^4$ each represent hydrogen or lower alkyl, and $R^5$ is a group of formula (A) or (B) or (C): $R^8$—$CH_2$—$CH_2$— or (D) or (E): $R^9OCH_2CHOHCH_2$— or (F): $R^9OCH_2CH_2$— and their pharmaceutically acceptable salts are 5-HT$_{1A}$ binding agents and may be used, for example, as anxiolytics.

18 Claims, No Drawings

AMIDE DERIVATIVES AS 5-HT$_{1A}$ LIGANDS

This application is a 371 of PCT/61394/00455 filed Mar. 9, 1994.

This invention relates to novel amide derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of general formula (I)

$$R^5NR^4CH_2CR^3R^{3'}N\begin{matrix}R^1\\ \\COR^2\end{matrix} \quad (I)$$

and the pharmaceutically acceptable salts thereof.

In formula (I)

$R^1$ is a mono or bicyclic heteroaryl radical, $R^2$ is cycloalkyl, $R^3$, $R^{3'}$ and $R^4$ each represent hydrogen or lower alkyl, and $R^5$ is a group of formula (A)

where X is —(CH$_2$)$_n$—, —OCH$_2$— or —SCH$_2$—, m is 0 or 1, n is 1, 2 or 3 and p is 0 or 1 such that (m+p) is 1 and that (m+n) is 1, 2 or 3, $R^6$ is hydrogen, lower alkyl, lower alkoxy, hydroxy, halogen, trifluoromethyl, (lower)alkoxycarbonyl, carboxamido, nitro, cyano, amino, (lower)alkylamino, di(lower)alkylamino or (lower) alkylcarbonyl, $R^{6'}$ is hydrogen or halogen when X is —(CH$_2$)$_n$— and $R^{6'}$ is hydrogen when X is —OCH$_2$— or —SCH$_2$—, $R^7$ is hydrogen or lower alkyl or (B)

where Y is —O—, —S— or —CH$_2$—,

Z represents a heteroaromatic ring fused on to the non-aromatic ring containing the Y group and $R^6$ is as defined above and one or more $R^6$ groups may be attached to the heteroaromatic ring and/or the non-aromatic ring or $$R^8—CH_2CH_2— \quad (C)$$

where $R^8$ is a monocyclic or bicyclic heteroaryl group or (D)

where $R^6$ is as defined above and the indicated 7, 8 positions may optionally be fused with a heteroaromatic ring or a further aromatic ring or $$R^9OCH_2CHOHCH_2— \quad (E)$$

where $R^9$ is a mono or bicyclic aryl or bicyclic heteroaryl group or $$R^9OCH_2CH_2— \quad (F)$$

where $R^9$ is as defined above.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, isobutyl, tert-butyl, pentyl and isopentyl.

Examples of cycloalkyl groups are groups containing 3 to 8 carbon atoms e.g. cyclopentyl, cyclohexyl and cycloheptyl.

When used herein "aryl" means an aromatic radical having 6 to 12 carbon atoms (e.g. phenyl or naphthyl) which optionally may be substituted by one or more substituents. Preferred substituents are lower alkyl, lower alkoxy (e.g. methoxy, ethoxy, propoxy, butoxy), halogen (e.g. chlorine), halo(lower)alkyl (e.g. trifluoromethyl), nitro, nitrile, amido, (lower)alkoxycarbonyl, amino, (lower)alkylamino and di(lower)alkylamino.

The term "heteroaryl" refers to an aromatic radical containing one or more (e.g. 1, 2 or 3) hetero ring atoms (e.g. oxygen, nitrogen, sulphur) and which may be optionally substituted by one or more substituents. Examples of suitable substituents are given above in connection with "aryl" radicals. The heteroaryl radical may, for example, contain 5 to 10 ring atom. Unless specified otherwise the heteroaryl radical is preferably mono- or bicyclic. A monocyclic radical may, for example, contain 5 to 7 ring atoms. Preferably the hetero ring contains a nitrogen atom with or without one or more further hetero atoms. Examples of heteroaryl groups include, for example, pyridinyl, pyfimidinyl, pyrazinyl, quinolinyl, isoquinolinyl and indolyl each of which may be optionally substituted as mentioned above.

When a "heteroaromatic ring" is fused on to a non-aromatic ring (as in formula B) or is fused on to an aromatic ring (as in formula D) the "heteroaromatic ring" may be a fused "heteroaryl" group where heteroaryl is defined above.

Examples of the preferred meanings of the various substituents in formula (I) are given below:

$R^1$ is pyfidinyl, particularly 2-pyridinyl, $R^2$ is cyelohexyl, $R^3$ is hydrogen and $R^{3'}$ is hydrogen or lower alkyl (e.g. methyl), $R^4$ is preferably hydrogen, methyl or propyl, A is preferably a group of formula:

where $R^6$ is as defined above, particularly lower alkoxy,

B is preferably a group of formula:

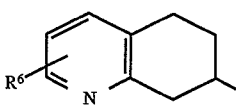

where $R^6$ is as defined above.

C is preferably a group of formula

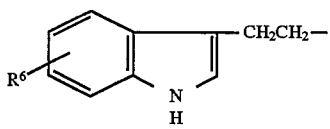

where $R^6$ is as defined above, particularly lower alkoxy,

D is preferably a group of formula

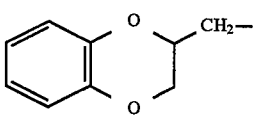

E is preferably a group of formula

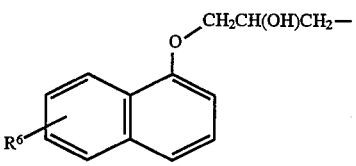

where $R^6$ is as defined above,

F is preferably a group of formula

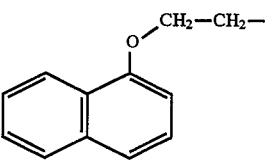

The compounds of the invention may be prepared by methods known in the art from known starting materials or starting materials that may be prepared by conventional methods.

One method of preparing the compounds of the invention comprises the reductive amination of a compound of formula

$R^5NHR^4$      (II)

(where $R^5$ and $R^4$ are as defined above) with an aldehyde of formula

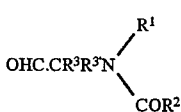      (III)

(where $R^1$, $R^2$, $R^3$ and $R^{3'}$ are as defined above) eg by reacting the compounds of formula (II) and (III) in the presence of a reducing agent (e.g. a hydride reducing agent such as sodium triacetoxyborohydride) or reacting the compounds of formula (II) and (III) together followed by reduction, eg using catalytic hydrogenation.

A second method of preparing the compounds of the invention comprises acylating an amine of formula $R^5NR^4CH_2CR^3R^{3'}NHR^1$      (IV)

(where $R^1$, $R^3$, $R^{3'}$, $R^4$ and $R^5$ are as defined above) with an acid of formula $R^2COOH$      (V)

where $R^2$ is as defined above or with an acylating derivative thereof. Examples of acylating derivatives include the acid halides (e.g. chlorides) azides, arthydrides, imidazolides (e.g. obtained from carbonyldiimidazole), activated esters or O-acyl ureas obtained from a carbodiimide such as a dialkylcarbodiimide particularly cyclohexyl-carbodiimide. In the compound of formula (IV) $R^4$ is preferably lower alkyl. If it is desired to prepare a compound of the invention in which $R^4$ is hydrogen it may be necessary to use a compound of formula (IV) in which $R^4$ is an amine protecting group and to remove the protecting group after the acylation reaction.

The starting compounds of formula (IV) may be prepared by reductive amination of a compound of formula (II) above with an aldehyde of formula

      (VI)

where $R^1$, $R^3$, $R^{3'}$ are as defined above and $R^{10}$ is hydrogen or, preferably, an amino protecting group (e.g. an urethane such as tert-butyloxycarbonyl), in presence of a reducing agent (e.g. a hydride reducing agent such as sodium triacetoxyborohydride) followed by deprotection of the amino group. When $R^{10}$ is, for example, tert-butyloxycarbonyl the protecting group may be removed by treatment with trifluoracetic acid or dilute hydrochloric acid.

A third method of preparing the compounds of the invention comprises alkylating an amide of formula

      (VII)

(where $R^1$ and $R^2$ are as defined above) with an alkylating agent providing the group $R^5NR^4CH_2CR^3R^{3'}-$ The alkylating agent may be, for example a compound of formula $R^5NR^4CH_2CR^3R^{3'}Q$      (VIII)

(where $R^3$, $R^{3'}$, $R^4$ and $R^5$ are as defined above and Q is a leaving group such as a halogen (e.g. bromine) or an ester (e.g. a tosylate or trifluoromethylsulphonate). In this process $R^4$ is preferably lower alkyl.

A fourth method of preparing the compounds of the invention comprises heteroarylating a compound of formula $R^5NR^4CH_2CR^3R^{3'}NHCOR^2$      (IX)

(where $R^2$, $R^3$, $R^{3'}$, $R^4$ and $R^5$ are as defined above) with a compound providing the heteroaryl group $R^1$. For example the reaction can be carried out with a fluoro compound of formula $R^1F$ in the presence of a strong non-nucleophilic base (e.g. lithium diisopropylamide). When $R^1$=2-pyridyl or $R^1$=4 pyridyl, the reaction is preferably carried out with a 2-fluoro- or 4- fluoropyridine-N-oxide followed by deoxygenation of the product pyridine-N-oxide with a reducing agent such as phosphorus trichloride.

If in any of the other processes mentioned herein, a substituent on the group $R^5$ is other than the one required the substituent may be converted to the desired substituent by known methods. A substituent on $R^5$ may also need protecting against the conditions under which the reaction is carried out. In such a case the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphufic, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different steroisomefic forms. The compounds can be for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. The compounds particularly bind to receptors of the $5\text{-HT}_{1A}$ type. The compounds of the invention can be used for the treatment of CNS disorders, such as anxiety in mammals, particularly humans. They may also be used as antidepressants, antipsychotics, hypotensives and as agents for regulating the sleep/wake cycle, feeding behaviour and/ or sexual function and for treating cognition disorders.

The compounds of the invention are tested for $5\text{-HT}_{1A}$ receptor binding activity in rat hippocampal membrane homogenate by the method of B S Alexander and M D Wood, J Pharm Pharmacol, 1988, 40, 888–891.

The compounds are tested for $5\text{-HT}_{1A}$ receptor antagonism activity in a test involving the antagonism of 5-carboxamidotryptamine in the guinea-pig ileum in vitro (based upon the procedure of Fozard et al. Br J Pharmac, 1985, 86, 601P).

The invention also provides a pharmaceutical composition comprising a compound of formula I or a pharmaceutically acceptable acid addition salt thereof in association with a pharmaceutically acceptable carrier. Any suitable carrier known in the an can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%. preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressufised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweetners, flavouring agents, suspending agents, thickening agents, colours, viscosity regulators, stabilisers or osmo-regulators. Suitable examples of liquid carriers for oral and parenteral administration include water (particularly containing additives as above. e.g. cellulose derivatives, preferably sodium carboxymethyl cellulose solution, alcohols, e.g. glyeerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compostions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

N-(3-(N'-(1,2,3,4-Tetrahydro-8-methoxynaphth-2-yl) methylamino)-2-propyl) N-(2-pyridinyl) cyclohexanecarboxamide A stirred suspension of potassium hydride, 35 wt. % suspension in mineral oil (0.01 mol) in dimethylformarnide (DMF) (100 ml) is treated dropwise under argon with N-(3-(N'-(1,2,3,4-tetrahydro-8-methoxynaphth-2-yl) methylamino)-2-propyl) N-(2-pyridinyl)amine (0.01 mol) in DMF (100 ml), after 1 h treated dropwise with cyclohexanecarbonyl chloride (0.01 mol), after 1 h treated dropwise with water (500 ml), acidified with 2N-HCl, washed with hexane (3×300 ml), basified with 2N-NaOH, and extracted with ethyl acetate (3×300 ml). The extracts are washed with brine (500 ml), dried ($Na_2SO_4$), and evaporated in vacuo. The residue is purified by chromatography [silica; ethyl acetate—ethanol (200:1)] to give the product as a colourless solid.

EXAMPLE 2

N-(3-(N'-(5,6,7,8-Tetrahydroquinolin-7-yl) methylamino)-2-propyl) N-(2-pyridinyl) cyclohexanecarboxamide This compound is prepared using the procedure of Example 1 with N-(3-(N'-(5,6,7,8-tetrahydroquinolin 7-yl) methylamino)-2-propyl)-N-(2-pyridinyl)amine in place of the amine reagent.

EXAMPLE 3

N-(3-(N'-(2-(3-(5-Methoxyindolyl)ethyl)) methylamino)-2-propyl) N-(2-pyridinyl) cyclohexanecarboxamide This compound is prepared using the procedure of Example 1 with N-(3-(N'-(2-(3-(5-methoxyindolyl) ethyl)) methylamino)-2-propyl)-N-(2-pyridinyl)amine in place of the amine reagent.

EXAMPLE 4

N-(3-(2-(2,3-Dihydro-1,4-benzodioxinyl) methylamino)-2-propyl)-N(2-pyridinyl) cyclohexanecarboxamide A solution of 2,3-dihydro-1,4-benzodioxin-2-ylmethylamine (0.01 mol) and N-(1-(1-formyl) ethyl)-N-(2-pyridinyl)cyclohexanecarboxamide (0.011 mol)in 1,2-dichloroethane (50 ml) is treated with sodium triacetoxyborohydride (0.005 mol) under argon. Acetic acid (0.01 mol is added and the mixture stirred for 18 h, washed with water (2×50 ml), dilute aqueous sodium carbonate (50 ml), and water (50 ml), dried ($MgSO_4$), and evaporated in vacuo. The residue is purified by chromatography. (alumina; ethyl acetate—methanol) to give the product.

EXAMPLE 5

N-(4-Aza-6-hydroxy-7-(1-naphthyloxyl)-2-heptyl)- N-(2-pyridinyl) cyclohexanecarboxamide This compound is prepared using the procedure of Example 4 with 2-hydroxy-3-(1-naphthyloxy) 1-propylamine in place of the amine component.

EXAMPLE 6

N-(4-Aza-6-(1-naphthyloxy)-4-propyl-2-hexyl)-N- (2-pyridinyl) cyclohexanecarboxamide This compound was prepared following the procedure of Example 1 with N-(4-aza-6-(1-naphthyloxy) 4-propyl-2-hexyl)pyridine-2-amine instead of the amine reagent.

EXAMPLE 7

N-(2-(N'-(2-(2,3-Dihydro-1,4-benzodioxinyl)methyl) methylamino)ethyl)-N-(2-pyridinyl) cyclohexanecarboxamide A mixture of N-(2-(N'-(2-(2,3-dihydro-1,4-benzodioxinyl)methyl)-methylamino)ethyl)pyridine-2-amine (2.20 g, 7.35 mmol), cyclohexanecarbonyl chloride (1.08 g, 7.35 mmol), 4-(dimethylamino)pyridine (catalytic mount) and diisopropylethylamine (0.95 g, 7.35 mmol) in dichloromethane (30 ml) was stirred over the weekend. The reaction mixture was diluted with dichloromethane (30 ml), washed with water (30 ml), dried ($Na_2SO_4$) and concentrated under reduced pressure to afford an oil. The crude oil was chromatographed on alumina, eluting with ethyl acetate:hexane (1:1 to 3:1) to give an oil (1.22 g). A sample of the oil (0.50 g) was dissolved in diisopropylether and acidified with ethereal hydrogen chloride to afford the hydrochloride salt of the title compound as an off-white solid (0.39 g) mp=83.5°–88° C. $^1$H NMR $\delta_H$ (200 MHz; $CDCl_3$) 0.8–1.8 (10 H, m) and 2.22 (1 H, tt) (cyclohexyl); 2.31 (3 H, s, NMe); 2.6 (2 H, m) and 3.9 (2 H, m ($NCH_2CH_2N$) 2.7 (2 H, m, $NCH_2$); 4.1–4.3 (3 H, m, $OCH_2CH$); 6.7–6.9 (4 H, m, benzodioxan); 7.2–7.3 (2 H, m pyridine H3 and H5); 7.74 (1 H, dt, pyridine H4); and 8.51 (1 H, dd, pyridine H6).

EXAMPLE 8

N-(2-(N'-(7-(5,6,7,8-Tetrahydroquinolinyl)) methylamino)ethyl)-N-(2-pyridinyl) cyclohexanecarboxamide (a) N-(2-Pyridinyl)-2-(N'-(7-(5,6,7,8-tetrahydroquinolinyl))methylamino)acetamide A solution of N-methyl-5,6,7,8-tetrahydroquinoline-7-amine (7.08 g, 12.8 mmol), N-(2-pyridyl) 2-chloroacetamide (2.19 g, 12.8 mmol) and diisopropylethylamine (1.66 g, 12.8 mmol) in N,N-dimethylformamide (70 ml) was stirred at room temperature overnight. The reaction mixture was poured into water (200 ml) and washed with ethyl acetate (2×100 ml). The combined organic phases were washed with brine (100 ml), water (100 ml), dried ($MgSO_4$) and concentrated to afford an oil. The crude oil was chromatographed on alumina, gradient eluting with ethyl acetate:hexane (1:1) and ethyl acetate to give the title compound of step (a) as an oil (2.67 g).

(b) N-Methyl-N-(2-(2-pyridinylamino)ethyl(-5,6,7, 8-tetrahydroquinoline-7-amine

A solution of the product of step (a) (1.70 g, 5.74 mmol) and borane-methyl sulphide complex in toluene (2.0 M, 8.60 ml, 17.2 mmol) in tetrahydrofuran (15 ml) was heated under reflux for 3 h. Methanol (5 ml) was added dropwise to the cooled (0° C.) reaction mixture which was subsequently concentrated under reduced pressure. The residue was dissolved in a mixture of water (10 ml) and concentrated hydrochloric acid (10 ml). The solution was heated under reflux for 40 min, cooled (0° C.) and basified with aqueous sodium hydroxide (2 M). The basic solution was washed with ethyl acetate (3×30 ml) and the combined organic phases washed with brine (30 ml), water (30 ml), dried ($MgSO_4$) and concentrated to give the title compound of step (b) as an oil (1.26 g).

(c) N-(2-(N'-(7-(5,6,7,8-Tetrahydroquinolinyl))methylamino)ethyl-N-(2-pyridinyl)cyclohexanecarboxamide A solution of the product of step (b) (1.26 g, 4.46 mmol), cyclohexanecarbonyl chloride (0.65 g, 4.46 mmol), diisopropylethylamine (0.58 g, 4.46 mmol) and a catalytic amount of 4-N,N-dimethylaminopyridine in dichloromethane (15 ml) was stirred overnight at room temperature. The separated organic phase was washed with water (15 ml), dried (MgSO$_4$) and concentrated to afford an oil (1.28 g). The crude oil was chromatographed on alumina, gradient eluting with ethyl acetate:hexane (5:4) and ethyl acetate to give an oil. The oil was dissolved in ethyl acetate and acidified with ethereal hydrogen chloride to afford an off-white hygroseopic solid. The solid was redissolved in isopropanol, concentrated and triturated with ethyl acetate to afford the dihydrochloride salt of the title compound as a hygroscopic pale-yellow powder (0.25 g) mp=140°–145° C. $^1$H NMR $\delta_H$ (200 MHz; (CD$_3$)$_2$SO) 0.8–1.8 (10 H, m) and 2.3 (1 H, m) (cyclohexyl); 2.0 (1 H, m), 2.4 (1 H, m), 3.0–3.8 (4 H, m) and 3.9 (1 H, m) (tetrahydroquinoline); 2.85 (3 H, br. s, NMe); 3.0–3.8 (2 H, m) and 4.15 (2 H, m) (NCH$_2$CH$_2$N); 7.45 (1 H, dd, pyridine H5); 7.63 (1 H, d, pyridine H3); 7.85 (1 H, dd, tetrahydroquinoline H3); 8.00 (1 H, dt, pyridine H4); 8.34 (1 H, d, tetrahydroquinoline H4); 8.63 (1 H, dd, pyridine H6); and 8.70 (1 H, d, tetrahydroquinoline H2).

We claim:

1. A compound of the general formula

R$^5$NR$^4$CH$_2$CR$^3$R$^{3'}$N$\diagdown^{R^1}_{COR^2}$ or a pharmaceutically acceptable salt thereof
wherein
R$^1$ is pyridinyl,
R$^2$ is C$_3$–C$_8$ cycloalkyl,
R$^3$,R$^{3'}$ and R$^4$ each represent hydrogen or C$_1$–C$_6$ alkyl,
R$^5$ is

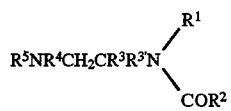, 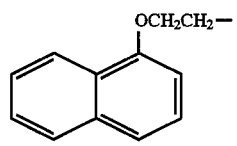,

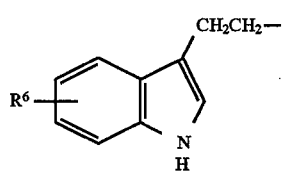

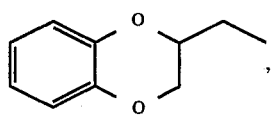

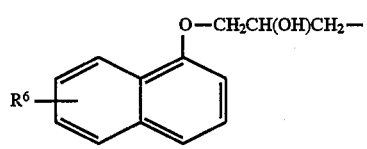 or

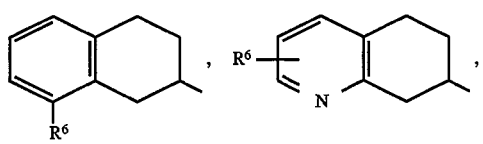

R$^6$ is hydrogen, C$_1$–C$_6$ alkyl, C$_1$–C$_6$ alkoxy, hydroxy, halogen trifluoromethyl, C$_1$–C$_6$ alkoxycarbonyl, carboxamido, nitro, cyano, amino, C$_1$–C$_6$ alkylamino, di-C$_1$–C$_6$ alkylamino or C$_1$–C$_6$ alkylcarbonyl.

2. A compound according to claim 1 wherein R$^1$ is 2-pyridinyl; and R$^2$ is cyclohexyl.

3. A compound as claimed in claim 2 wherein R$^5$ is a group of formula

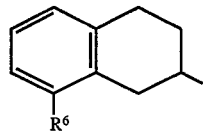

(where R$^6$ is as defined in claim 1).

4. A compound as claimed in claim 2 wherein R$^5$ is a group of formula

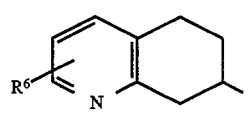

5. A compound as claimed in claim 2, wherein R$^5$ is a group of formula

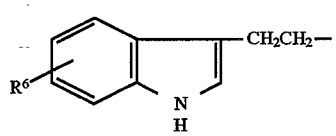

(where R$^6$ is as defined in claim 1).

6. A compound as claimed in claim 2 wherein R$^5$ is a group of formula

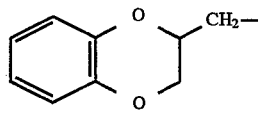

7. A compound as claimed in claim 2 wherein R$^5$ is a group of formula

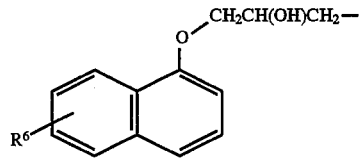

(where R$^6$ is as defined in claim 1).

8. A compound as claimed in claim 2 wherein R$^5$ is a group of formula

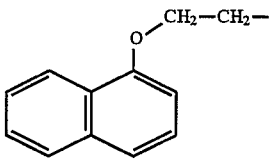

9. A compound as claimed in claim 2 which is

N-(3-(N'-(1,2,3,4-tetrahydro-8-methoxynaphth-2-yl) methylamino)-2-propyl) N-(2-pyridinyl) cyclohexanecarboxamide or N-(3-(N'-(5,6,7,8-tetrahydroquinolin-7-yl)methylamino)-2-propyl)-N-(2-pyridinyl) cyclohexanecarboxamide or N-(3-(N'-(2-(3-(5-methoxyindolyl)ethyl))methylamino)-2-propyl)-N-(2-pyridinyl) cyclohexanecarboxamide or N-(3-(2-(2,3-dihydro-1,4-benzodioxinyl)methylamino)-2-propyl)-N-(2-pyridinyl) cyclohexanecarboxamide or N-(4-aza-6-hydroxy-7-(1-naphthyloxyl)-2-heptyl)-N-(2-pyridinyl) cyclohexanecarboxamide or N-(4-aza-6-(1-naphthyloxy)-4-propyl-2-hexyl)-N-(2-pyridinyl) cyclohexanecarboxamide or N-(2-(N'-(2-(2,3-dihydro-1,4-benzodioxinyl)methyl) methylamino)ethyl-N-(2-pyridinyl) cyclohexanecarboxamide or N-(2-(N'-(7-(5,6,7,8-tetrahydroquinolinyl))methylamino) ethyl)-N-(2-pyridinyl) cyclohexanecarboxamide or a pharmaceutically acceptable acid addition salt thereof.

10. A pharmaceutical composition for us as 5HT$_{1A}$ antagonist comprising a compound claimed in claim 2 in association with a pharmaceutically acceptable carrier.

11. A compound of claim 2 which is N-(3-(N'-(1,2,3,4-tetrahydro-8-methoxynaphth-2-yl) methylamino)-2-propyl)-N-(2-pyridinyl)cyclohexanecarboxamide or a pharmaceutically acceptable salt thereof.

12. A compound of claim 2 which is N-(3-(N'-(5,6,7,8-tetrahydroquinolin-7-yl)methylamino) 2-propyl)-N-(2-pridinyl)cyclohexanecarboxamide or a pharamceutically acceptable salt thereof.

13. A compound of claim 2 which is N-(3-(N'-(2-(3-(5-methoxyindolyl)ethyl))methylamino) 2-propyl)-N-(2-pyridinyl)cyclohexane-carboxamide or a pharmaceutically acceptable salt thereof.

14. A compound of claim 2 which is N-(3-(2-(2,3-dihydro-1,4-benzodioxinyl)methylamino) 2-propyl)-N-(2-pyridinyl)cyclohexanecarboxamide or a pharmaceutically acceptable salt thereof.

15. A compound of claim 2 which is N-(4-aza-6-hydroxy-7-(1-naphthyloxyl)-2-heptyl) N-(2-pyridinyl) cyclohexanecarboxamide or a pharmaceutically acceptable salt thereof.

16. A compound of claim 2 which is N-(4-aza-6-(1-naphthyloxy)-4-propyl-2-hexyl) N-(2-pyridinyl) cyclohexanecarboxamide or a pharmaceutically acceptable salt thereof.

17. A compound of claim 2 which is N-(2-(N'-(2-(2,3-dihydro-1,4-benzodioxinyl)methyl) methylamino)ethyl-N-(2-pyridinyl)cyclohexanecarboxamide or a pharmaceutically acceptable salt thereof.

18. A compound of claim 2 which is N-(2-(N'-(7-(5,6,7,8-tetrahydroquinolinyl))methylamino) ethyl)-N-(2-pyridinyl)cyclohexanecarboxamide or a pharmaceutically acceptable salt thereof.

* * * * *